United States Patent [19]

Combes et al.

[11] 4,352,812
[45] Oct. 5, 1982

[54] METHOD OF COMBATING CERCARIAE USING CERTAIN AMPHOTERIC SURFACE ACTIVE AGENTS

[75] Inventors: Claude Combes, Perpignan; Jean Arnaudis; Germaine Arnaudis, both of Castres; Lucien Marcou, St-Maur, all of France

[73] Assignee: Produits Chimiques de la Montagne Noire, Paris, France

[21] Appl. No.: 178,984

[22] Filed: Aug. 18, 1980

[30] Foreign Application Priority Data

Aug. 31, 1979 [FR] France ................................ 79 21941
Apr. 14, 1980 [FR] France ................................ 80 08533

[51] Int. Cl.³ ...................... A01N 43/50; A01N 37/30
[52] U.S. Cl. ................................ 424/273 R; 424/316; 252/107

[58] Field of Search ........................... 424/273 R, 316; 252/107

[56] References Cited

U.S. PATENT DOCUMENTS 3,366,671  1/1968  Cowen et al. ................. 260/501.12
3,555,079  1/1971  Marumo ......................... 260/501.13
3,974,208  8/1976  Dudzinski et al. ............. 260/501.11

FOREIGN PATENT DOCUMENTS 1162133 10/1955 France.
7300138  1/1973 France.

Primary Examiner—Leonard Schenkman
Attorney, Agent, or Firm—Eyre, Mann, Lucas & Just

[57] ABSTRACT

Method for combating cariae, the carrier organisms of bilharziasis, by means of amphoteric surface-active products of the betaine or imidazoline type which can be included in cakes of toilet or household soap.

4 Claims, 1 Drawing Figure

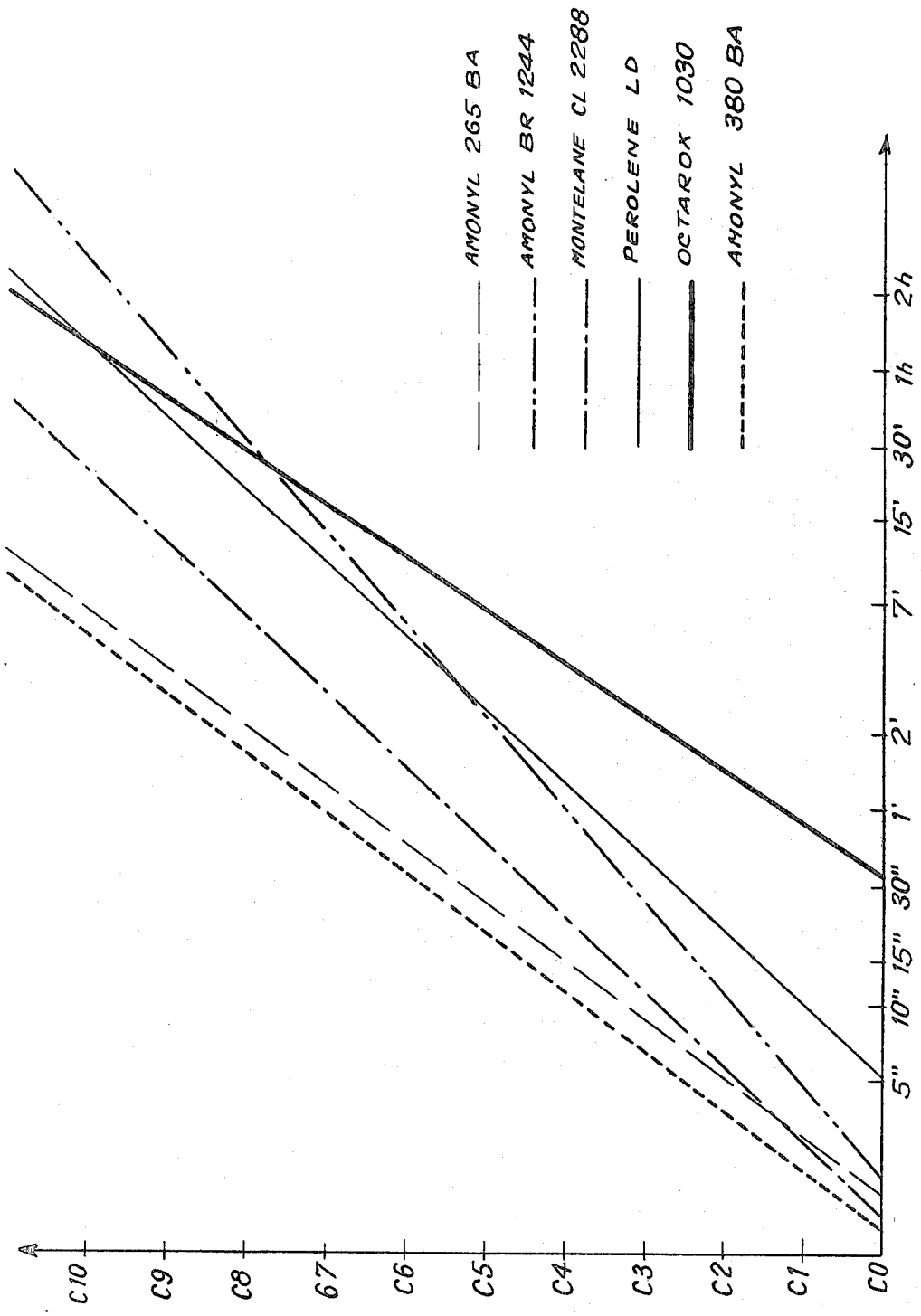

METHOD OF COMBATING CERCARIAE USING CERTAIN AMPHOTERIC SURFACE ACTIVE AGENTS

The present invention relates to a method of combating cercariae, the causative organisms of bilharziasis, by means of amphoteric surface-active products of the betaine or imidazoline type which can be included in cakes of household soap.

Human schistosomiasis or bilharziasis is the second most prevalent human disease. The number of humans suffering from this disease ranges from 200,000,000 to 400,000,000 and the disease is becoming more widespread.

Four main types of schistosomiasis exist in tropical or sub-tropical countries; the most widespread is caused by schistosoma mansoni and is common in Africa and South America; two others are only African, the fourth only exists in the Far East.

Schistosomiasis are diseases with a carrier; these are, in all cases, aquatic molluscs of tropical and sub-tropical fresh water. The carrying is achieved from the man to the mollusc by a first larval form known as miracidium, and that from the mollusc to the man by a second larval form known as cercariae. This larval form, the cercariae, penetrates the human skin when the latter comes into contact with the infested water, for example, on bathing, washing of clothes or any other reason for contact.

The methods of combating the schistosomiasis are either therapeutic, or against the host or carrier.

The therapeutic methods are only lasting from persons who are no longer in contact with infested water.

The other methods are either combating the molluscs, or the carriers in larval form.

The most promising first against schistosomiasis is integrated control, which has recourse both to therapeutics, to the fight against the hosts, to the use of cercaricides and to increasing the level of education and hygiene.

On the therapeutic level, there are a certain number of active medicaments against bilharziasis; unfortunately, these pharmaceutical products do not avoid reinfection of the treated individuals. It is hence indispensable to have means available, parallel to the medicine, which make possible the fight against the disease carriers.

The present invention hence relates to a method of combating the cercariae which are responsible for transmitting the bilharziasis to man; this method consists of adding to water containing the cercariae at least one amphoteric surface-active agent and more especially an amphoteric surface-active agent of the betaine or imidazoline type.

It is usual to classify surface agents according to their ionic activity, into anionic, cationic, non ionic or amphoteric derivatives.

The anionic surface agents are salts obtained by neutralization of molecules with a long fatty chain, which contain a grouping which is carboxyl, sulphonic by means of a mineral alkaline agent (soda, potassium . . . ) or organic (amine).

The cationic surface agents are salts obtained by neutralization of molecules with a long fatty chain, which contain one or several nitrogen atoms by means of a strong acid or a cationising agent (dimethyl sulphate, benzyl chloride . . . ), it being possible to include the nitrogen in a heterocycle: (pyridinium, imidazolinium salts).

The non ionic surface agents are products which do not ionize in water and whose solubility is due to hydroxyl groups or oxygen bridges (derivatives of ethylene oxide, polyalcohol esters).

The amphoteric surface agents are products which contain both one or several anionic groupings and one or several cationic groupings and which, according to the pH of their medium, can react as anionic or cationic surface agents (derivatives of alanine, glycin, betains, carboxylised derivatives of imidazolinium).

The surface active agents which can be used according to the present invention are amphoteric agents and more especially agents of the betaine or imidazoline type. The principal amphoteric surface agents which are known and can be used are the following:

Alkylbetaines and alkylamidobetaines;
The derivatives of imidazolinium, of which the most widely used commercial brand is Miranol;
The derivatives of glycin;
The derivatives of β-alanine;
The N-alkylaminobutyric derivatives;
The N-alkylaminosuccinates and N-Alkylaminopropionates.

The betaines have the general formula:

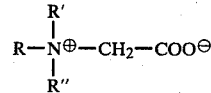

in which R is a linear or branched aliphatic fatty chain, consisting of 6-18 atoms of carbon, or a fatty chain radical, consisting of 8-24 atoms of carbon and an intermediate function which can be an amide group, an ether group, an ester group, etc., or an alkylphenyl radical whose fatty chain consists of 4-12 atoms of carbon; R' and R" are short aliphatic chains containing 1-5 carbon atoms, or hydroxymethyl, hydroxyethyl, hydroxypropyl groups.

The preparation of these alkylbetaines is usually achieved by reaction in an aqueous medium, between a tertiary amine and monochloracetic acid or its salts, according to the reaction:

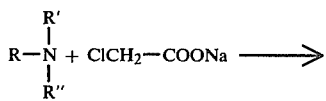

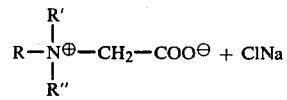

Instead of monochloracetic acid, it is possible to use monochlorinated acids with a greater molecular weight such as monochloropropionic acid, monochlorobutyric acid, etc.

In all cases, whether the reagent is an acid (or a salt of this acid,) the alkylbetaines are obtained in an aqueous solution containing a salt (most often sodium chloride).

If the initial tertiary amine is a fatty dimethylalkylamine, for example; laurylamine, oleylamine, stearylamine, etc., this reaction leads to products which are usually known as alkylbetaines, respectively: laurylbetaines, oleylbetaines, stearylbetaine etc.

If the initial tertiary amine is synthesized by reaction between a fatty acid and a diamine of the formula:

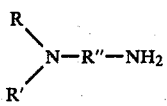

in which R, R' and R'' are aliphatic radicals containing 1-5 carbon atoms, a tertiaryamidoamine is obtained according to the reaction:

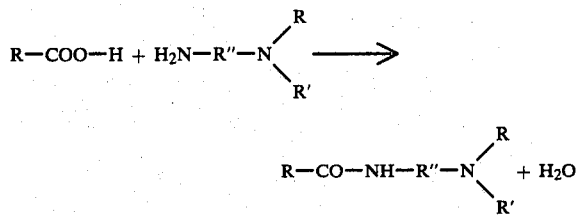

By condensation of this tertiary amine with monochloracetic acid, its salts or its esters, a betaine is obtained which includes, in its hydrophobic chain, an intermediate amide group.

These products, of which the formula is given below, are usually known as: alkylamidobetaines.

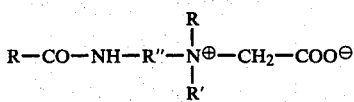

If the tertiary amine is obtained by condensation of two molecules of ethylene oxide on a fatty amine according to the reaction:

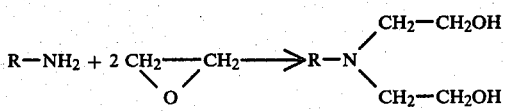

The betaine obtained is an alkyl-N-diethoxybetaine of the formula:

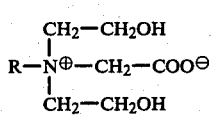

All these betaines are obtained in this manner and marketed in the form of aqueous solutions containing approximately 30–50% by weight of the surface active agent and a certain quantity (mostly the stoechiometric quantity) of a salt, for example, sodium chloride.

The amphoteric surface active agents which contains an imidazoline group are prepared from the product of the reaction of two molecules of fatty acid on a diamine of the formula:

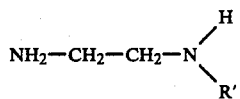

in which R' can be:

a hydrogen: it is then a question of ethylenediamine
an ethoxy group: it is an aminoethylethanolamine
an ethyleneamine group: it is then diethylenetriamine
a fatty aliphatic group: it is then a fatty diamine After amidation and elimination of a molecule of water, this reaction leads to an alkylimidazoline of the formula:

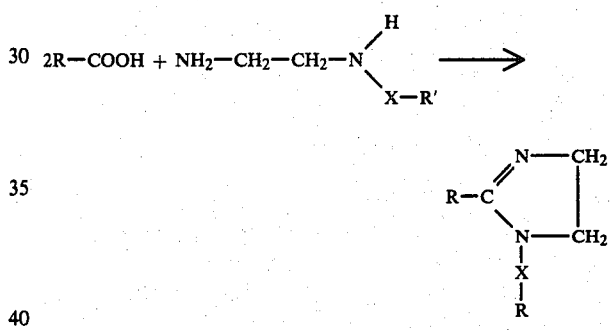

in which X can be:
—CO—NH—(CH$_2$)$_n$—CH$_2$

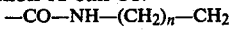

—CO—O—(CH$_2$)$_n$—CH$_2$, etc.

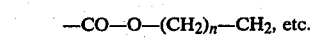

It is possible to synthesize an amphoteric surface agent from this dialkylimidazoline by reaction with monochloracetic acid, its salts or its esters. This reaction leads to a derivative of the formula:

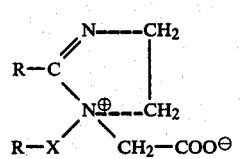

This structure is only given as an indication, for it is well known that alongside the imidazoline, diamide esters, ester imidazolines, ester amides, etc. are formed and that, owing to the instability of the imidazoline ring which can be partially hydrolised, there is also an amide of the formula:

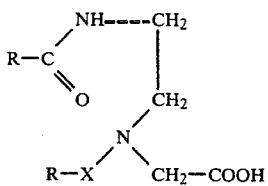

However, here again, as in the case of betaines, the ampho teric surface agent is obtained and marketed in the form of an aqueous solution which contains a salt, generally sodium chloride.

The investigation of the cercaricide activity of the surface agents was made both in vitro and in vivo.

The method in vitro consists of determining the time necessary for the inactivation of 50% of the cercariae, by putting equivalent batches in contact with surface active solutions of varying concentrations; in this manner the concentration of surface active agents which activates 50% of the cercariae ($CI_{50}$) present in the water is determined and the results are shown on diagrams on which the said concentration $CI_{50}$ is shown in the ordinate and the time necessary for this inactivation is shown on the abscissa.

The tests described here were carried out on Schistosona mansoni but it was possible to note in addition that the various Schistosona had comparable sensitivities with regard to surface active agents; the cercariae had proceeded from molluscs which had been bred in deep well water, with a hardness of 32.5 French degrees and pH 7.6. The tests were carried out at ambient temperature.

On the single FIGURE, the results of these tests are given; on this FIGURE the concentration $CI_{50}$ of the surface agent used is given in the ordinate, expressed in milliequivalent per liter (this is in order to be able to compare the molecular activity of each surface active agent investigated). The maximum concentration (Co) investigated corresponds to 300 meq/l; the weaker concentrations are obtained by dilution of half the preceeding concentration. Hence, $C_1$ represents the concentration (Co/2), that is 150 meq; the concentration $C_2 = (Co/4)$, that is 75 meq/l; the concentration $C_3 = (Co/8)$, i.e. 37.5 meq/l.

The logarithm of the time is given in the abscissa.

In the drawing, the names shown are chemically identified as follows:

Amonyl 265 BA—an amphoteric surface active agent of the alkyl betaine type.

Amonyl BR 1244—Dodecyldimethylbenzylammonium bromide.

Montelane CL 2288—Sodium laurylethersulphate.

Perolene LD—Sodium dodecylbenzenesulphonate.

Octarox 1030—Octylphenol condensed with 10 molecules of ethylene oxide.

Amonyl 380 BA—an amphoteric surface active agent of the alkyl betaine type.

The results obtained make it possible to ascertain in particular that the slopes of these curves are characteristic of the ionic activity of the surface active agent:
the anionic products, represented on this curve by MONTELANE CL 2288 (sodium laurylethersulphate) and PEROLENE LD (sodium dodecylbenzenesulphonate) have a cercaricide activity which decreases quite quickly with the concentration; the two curves have similar slopes;

The non ionic products, respresented by OCTAROX 1030 (octylphenol condensed with 10 molecules of ethylene oxide), have a weak cercaricide activity at strong concentration but which diminishes less rapidly than that of ionic products during dilution;

The cationic products, and here we have a surprise because these products are the most active on the germicide level: bactericide, fungacide, algicide, and have quite considerable activity at high concentration but which is rapidly reduced with dilution. They are represented here by AMONYL BR 1244 (dodecyldimethylbenzylammonium bromide). The activity of this product is zero below 3.5 ppm;

The amphoteric products are the best cercaricides at all concentrations; they are represented on this curve by AMONYL 265 BA and 380 BA.

This cercaricide activity is shown in the Table 1 below giving the average inactivation time of 50% of the cercariae concentration of 1 ppm.

It hence appears clear that if the surface agents of various types are active in vitro against the cercariae, the amphoteric surface agents, more precisely the betaine derivatives, are particularly active and hence of interest.

The results obtained are all the more of interest if it is considered that the less of infecting power of the cercariae takes place in time well before the total immobilisation of these cercariae.

For the tests in vivo, a standard quantity of cercariae is used to infest a batch of mice in the presence of the surface agent and an identical batch in the presence of water only, according to the Erickson technique. The control of the experiment is made in the 7th week, by perfusion of the venos hepato-mesenteric system by the technique of Duwall and Dewitt.

The difference between the tested subjects and the control subjects gives an exact indication of the effective limitations, due to the surface agents, in the penetration of the cercariae.

The white mice used are of the stock OF (1).

The control of the tests is carried out:
1. By counting of the cercariae which have not penetrated the skin, after the exposure of the mice;
2. By counting adult parasites 7 weeks after contamination;
3. In investigating the fertility of the adult parasites by counting the number of parasite eggs per milligramme of liver of the contaminated mice.

These contamination experiments are carried out at limit concentration of surface agents and for contact times of 15–60 minutes.

The results obtained are summarised in Table II below.

The results given in Table II below show that, whereas the various surface agents are active in the combat against contamination by cercariae, the amphoteric agents (represented hereby AMONYL 265 BA) are the most active.

Hence, if the invention concerns the utilisation of surface agents for the fight against cercariae, it is clear that the surface agents which are of greatest interest are the amphoteric products.

The implementation of the invention consists of adding to water which contains or which is likely to contain cercariae at least one surface agent of the amphoteric type and more especially of the alkyl or amidoalkylbetaine type. The quantities of surface agents to be used are generally small, their concentration in the infected water being for example between 0.5 and 10 ppm inclusive. The methods to be used for adding the surface agent to the infected water can be extremely varied. Hence the surface agent can be poured into the infected water in pure form or in a solution of known concentration, the surface agent can also be incorporated in various washing products (including soaps).

Now it has been found that it was possible and advantageous to use these amphoteric agents in solid products such as toilet soap and washing soap. To do this, it is suitable to have amphoteric surface active agents of the betaine or imidazoline type in the salt (generally sodium chloride) which accompanies them when these products are made according to known processes.

It has been found that it was possible to obtain amphoteric surface active agents of the betaine or imidazoline type without a salt being present provided the reaction is carried out with monochloracetic acid, its salts or its esters in a nonaqueous polar organic solvent medium.

This solvent is to the best advantage an alcohol or dimethylformamide or dimethylsulphoxide. The tertiary amine (the case of betaines) or dialkyimidazoline (the case of imidazaline surface active agents,) is dissolved in the said solvent and to this solution is added monochloracetic acid or a salt or a ester of this acid. At the end of the reaction, the molecule of hydrochloric acid or a salt which is formed can be easily eliminated.

Hence a stable solution of the amphoteric surface active product is obtained, free from the salt.

The solvent can be partially or totally eliminated by distillation (possibly under vacuum), preferably in an evaporator with a thin layer or in a rotary evaporator.

The surface active agents of the betaine or imidazoline type prepared in this manner can be used in solid products, such as cakes of toilet soap or washing soap, which are known and used for their surface active properties. These solid products can be on a soap base (that is sodium salts of fatty acids) or based on other surface active agents (in the case of syndets detergents).

In solid products on a soap base, the amphoteric surface active agents according to the invention are used in a quantity between 10 and 50% inclusive by weight of the mixture and preferably between 15 and 30% by weight of the mixture.

In the products based on other surface active agents (syndets) only amphoteric surface active agents according to the invention can be used (especially in mixture) or mixtures of amphoteric agents according to the invention with other surface active agents.

The synthetic cakes of toilet soap (syndets) are prepared at present for dermatological purposes, for persons with sensitive skin or who are allergic to soap of which they do not tolerate the alkalinity. These syndets are prepared from surface agents which are well tolerated by the skin and give washing solutions of neutral pH or slightly acid.

These syndets have a certain number of advantages over soap:
   Less marked aggression towards the skin,
   Neutral or slightly acid pH,
   Insensitivity to hard waters, which avoids the formation of a precipitate or "scum",
   Improved stability of perfumes which, owing to this, can be used in a smaller proportion.

The existing syndets usually consist of:
   Fillers,
   superfatting and plasticising agents,
   additives which improve brilliancy and lubricate the paste during plasticising,
   Colouring agents,
   Perfumes.

The surface agents most widely used for the preparation of syndets are, among others:
   potassium, sodium, alkylsulphate etc.
   alkylsulphoacetates,
   hamisulphosuccinates,
   acylglutamates, etc.

The fillers include:
   Agents containing starch: starches, rice starch, maize starch, etc.
   Mineral fillers: colloidal silica, bentonite, potassium chloride, etc.
   Sugars: glucose, etc., The plasticising or superfatting products are based on:
   alkylolamides of fatty acids,
   aminoxides,
   heavy fatty alcohols.

The brilliancy and lubrication on plasticising are obtained by addition of palmitic acid or stearic acid.

The formulation of these various ingredients with a view to preparing bases for syndets is directed in order that the mechanical properties of the products make it possible for them to pass through the plasticising machine and the mould and in order that the toilet soap has the usual characteristics of soap: brilliancy, softness, resistance to slaking, lathering power, etc.

Mixed cakes of toilet soap containing soap and synthetic surface agents, which are easier to prepare on the level of the formulation and the technological level, have also been manufactured, unfortunately these mixed toilet soaps do not have all the dermatological properties of synthetic cakes of soap; in fact, their pH is of necessity alkaline owing to the presence of soap and the action of the latter is reinforced by the presence of the synthetic surface active product.

Finally, it has been found that these cakes of toilet soap or household soap (whether soaps or syndets) containing the amphoteric agents according to the invention are a very valued form of source of amphoteric agent which is active against the cercariae.

The non limiting examples given below show, on the other hand, the activity of certain amphoteric agents against cercariae and, on the other hand, the soaps and syndets which can be used in combating cercariae.

EXAMPLE 1

A copra alkylbetaine with a chain in $C_8$-$C_{18}$ is prepared by reaction in isopropanol between an alkyldimethylamine in $C_8$-$C_{18}$ obtained from a copra fatty amine and an excess of monochloracetate of soda.

The alkylbetaine obtained in separated from the sodium chloride formed and from the excess monochloracetate of soda by filtration. The result is a solution of alkybetaine in the isopropanol containing approximately 50% of dry extract, with a pH of approximately 8.

A quantity of this alkylbetaine corresponding to a concentration of 2 ppm of alkylbetaine was poured into a tank filled with water containing cercariae of Schistosoma mansoni.

The water treated in this manner was found to be completely innocuous to the various animals which were soaked in it.

The alkylbetaine prepared in this manner is mixed with a commercial detergent powder; the detergent mixture obtained was used in the usual manner for washing clothes with water containing cercariae; the clothes which had been washed were rinsed with non polluted water and the rinsing water was put in contact with various animals. No case of bilharziasis was found among the animals put in contact with this rinsing water.

EXAMPLE 2

Similar results to those described in Example 1 were obtained using instead of the alkylbetaine used in Example 1, (a) An alkylbetaine prepared as described in Example 1, but starting from heavy fraction of fatty acids of copra;
(b) An alkylamidobetaine obtained from methyl esters of total fatty acids of copra, dimethylaminopropylamine and monochlorecetate of soda;
(c) An alkylamidobetaine obtained as above in (b), but starting from heavy fraction of fatty acids of copra;
(d) An alkylamidobetaine obtained from methyl esters of total fatty acids of copra, dimethylaminoethylamine and monochloracetate of soda.

EXAMPLE 3

An alkylbetaine is prepared by condensation between a fatty amine obtained from total fatty acids of copra and monochloracetate of soda.

This solution of alkylbetaine in isopropanol is concentrated under vacuum in an evaporator with a thin layer (Luwa apparatus for example). The product obtained has the following characteristics:

| | |
|---|---|
| Dry extract | 96–97% |
| Salt content | ≦3% |
| Water | approx. 0.5% |
| Isopropanol | 1–2% |
| Free amine | approx. 2% |

This alkylbetaine appears as a cream coloured pasty solid, slightly pearly, which becomes liquid at a temperature between 120° and 130° C. inclusive.

EXAMPLE 4

An alkylbetaine in $C_{12}$–$C_{14}$ (chain known as lauric) is prepared according to the methods described in Example 3, but from a tertiary amine synthesised from a fatty acid in $C_{12}$–$C_{14}$ containing approximately 70 parts of lauric acid and 30 parts of myristic acid.

The alkylbetaine obtained has properties similar to those in Example 3; its appearance, is however, a little more waxy.

EXAMPLE 5

An alkylbetaine in $C_{16}$–$C_{18}$ (chain known as of tallow) is prepared according to the method described in Example 3, but from a fatty amine in $C_{16}$–$C_{18}$, prepared from tallow.

The alkylbetaine obtained has properties similar to those of Examples 3 and 4, but the wax obtained is harder and less adhesive.

EXAMPLE 6

A copra alkylamidobetaine (with a chain in $C_{12}$–$C_{18}$) is prepared by reaction between a heavy fraction of fatty acid of copra in $C_{12}$–$C_{18}$ dimethylaminopropylamine.

This reaction leads to an alkylamidopropyldimethylamine. This alkylamidoamine dissolved in isopropanol is put to react with monochloracetate of soda in excess and brought to an alkylamidobetaine in solution in isopropanol.

By filtering in order to separate the sodium chloride formed and the excess monochloracetate of soda, a solution in isopropanol is obtained which contains approximately 47% of this alkylamidobetaine.

This solution is concentration under vacuum, preferably in an apparatus of the rotary type or in a modified drying apparatus with a thin layer of the Luwa type.

The alkylamidobetaine in $C_{12}$–$C_{18}$ obtained has the following characteristics:

| | |
|---|---|
| Dry Extract | 97% |
| Sodium Chloride content | <2% |
| Water Content | Approx. 0.5% |
| Isopropanol Content | 2–3% |

This betaine appears as a pasty solid, chestnut coloured, whose melting point is between 150° and 160° C.

EXAMPLE 7

A lauric alkylamidobetaine is obtained according to the process described in Example 6, but starting from lauric acid.

The reaction with the monochlorecetate of soda is carried out in n-propanol.

The products obtained have the following characteristics:

| | |
|---|---|
| Dry Extract | Approx. 99% |
| pH in 5% solution in water | 7.25% |
| Salt content | <2% |

The product obtained is a relatively hard beige coloured wax which is malleable from 80° C. and melts at about 170° C.

EXAMPLE 8

A palmitic alkylamidobetaine is obtained according to the process desired in Example 6, but starting from palmitic acid.

The alkylamidobetaine obtained has the following characteristics:

| | |
|---|---|
| Dry Extract | 96-97% |
| pH in 5% solution in water | approx. 6 |
| Salt content | <3% |
| Isopropanol Content | 3-4% |

This products appears in the form of a hard brittle beige coloured wax, which melts at about 150° C.

EXAMPLE 9

A cake of soap containing alkylbetaine in $C_8-C_{18}$ is obtained by mixture of 50-90% of a sodium soap prepared from a mixture containing 20% of copra oil and 20% of tallow, and 10-50% of the alkylbetaine prepared according to the process described in Example 3.

The soap obtained can be coloured and perfumed according to the usual methods. After plasticising and putting through a mould it gives a brilliant oily cake which has preserved the usual qualities of soap, but which has in addition an inhibiting action with regard to the cercariae of bilharziasis.

EXAMPLE 10

A cake of soap containing alkylbetaine $C_{12}-C_{14}$ is obtained according to the process described in Example 9, but using betaine prepared according to the method of Example 4.

The cake of soap obtained has the same qualities as that described in Example 9.

EXAMPLE 11

A cake of soap containing alkylbetaine of tallow is obtained by mixing 50-90% sodium soap prepared from a mixture of 20% copra and 80% tallow, and 10-50% of alkylbetaine in $C_{16}-C_{18}$ prepared according to the process of Example 5.

The cake of soap obtained has sufficient characteristics and can contain greater quantities of betaine than the cakes of soap described in the preceding examples.

EXAMPLE 12

Cakes of soap containing alkylamidobetaines such as those described in Examples 6, 7 and 8 are obtained according to the process described in Example 9, but replacing the alkylbetaines by these products.

The cakes of soap obtained are easy to plasticise and after moulding, give smooth brilliant cakes of soap which have good inhibiting properties with respect to the cercariae of bilharziasis.

EXAMPLE 13

A dialkylamidoimidazoline, prepared from total fatty acids of copra and diethylenetriamine, is dissolved in isopropanol and treated by means of monochloracetate soda in excess. The sodium chloride formed and the monochloracetate of soda in excess are removed by filtration from the solution obtained.

The result is a 47% solution of ampho teric dialkylamidimidazoline in isopropanol, with the formula:

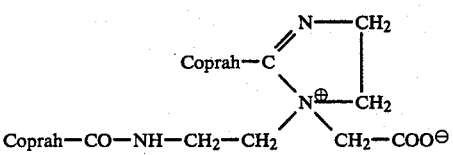

The isopropanol is eliminated by passing through an evaporator with a thin layer, under vacuum, of the Luwa type, for example, and the amphoteric imidazoline obtained has the following characteristics:

| | |
|---|---|
| Dry Extract | 90% |
| Water Content | <1.5% |
| Salt Content | <1.5% |
| pH in 5% solution 6-8. | |

This product is a chestnut coloured wax which is quite hard, which melts at about 55° C.

EXAMPLE 14

An amphoteric dialkylamidoimidazoline in $C_{16}$ is prepared according to the process described in Example 13, but using palmitic acid instead of total fatty acids of copra.

The product which has two fatty radicals in $C_{16}$ has the characteristics given below:

| | |
|---|---|
| Dry Extract | 97.3% |
| Water Content | <1.5% |
| Sodium Chloride | <1.5% |
| pH in 5% solution | 6-8 |

This amphoteric imidazoline appears in the form of a hard brittle solid, of beige colour, which is viscous at 75° C. and liquid above 95° C.

EXAMPLE 15

Totally synthetic bases for toilet or washing cake are obtained by mixing an alkylbetaine or an alkylamidobetane such as those described in Examples 3-8 with amphoteric dialkylamidoimidazolines prepared according to the methods described in Examples 13 and 14.

According to the mixtures and their proportions, the characteristics of these basis for syndets are as follows:

| Mixture | | Appearance | Lathering power |
|---|---|---|---|
| Alkylbetaine | Dialkylamidoimidazoline | | NF T 73.404 |
| $C_8-C_{18}$: 33,3% | $C_{16}$: 66,7% | Hard, adhering little | 180-150-120 |

| Mixture | | Appearance | Lathering power |
|---|---|---|---|
| $C_8$-$C_{18}$: 40% | $C_{16}$: 60% | hard, slightly adhering | 200-170-150 |
| $C_8$-$C_{18}$: 33,3% | copra: 66,7% | very soft | — |
| Alkylamidobetaine | Dialkylamidoimidazoline | | |
| $C_{12}$-$C_{18}$: 33,3% | $C_{16}$: 66,7% | hard, opaque, adhering little | 130-60-50 |
| $C_{12}$-$C_{18}$: 50% | $C_{16}$: 50% | hard, slightly adhering | 280-240-220 |
| $C_{12}$-$C_{18}$: 60% | $C_{16}$: 40% | not very hard, adhering | 330-300-260 |
| $C_{12}$-$C_{18}$: 25% | $C_{16}$: 75% | hard, adhering | — |
| $C_{12}$: 50% | $C_{16}$: 50% | hard, opaque, slightly adhering | 120-30-20 |
| $C_{12}$: 33,3% | Copra: 66,7% | very soft | — |

The mixtures of 30–40% of alkylbetaine in $C_8$-$C_{18}$ and of 60–70% of amphoteric dialkylamidoimidazoline $C_{16}$; those of 40–60% of alkylamidobetaine in $C_{12}$-$C_{18}$ and 60–40% of amphoteric dialkylamidoimidazoline in $C_{16}$ lead to basis of syndets which can easily be transformed into toilet or household cakes for adding various usual fillers,: perfume, colouring agent, etc., The cakes obtained are of agreeable texture, very lathery, well tolerated by the skin, insensitive to hard water; they can be kept at a slightly acid pH which is favourable to the protection of the skin. In addition to their dermatological properties, these syndets are endowed with inhibiting properties with regard to the cercariae of bilharziasis.

TABLE I

| Product | Length of life of cercariae in the presence of 1 ppm of the product |
|---|---|
| Dodecyldimethylbenzylammonium bromide | longer than 2 h 30 |
| Sodium Dodecylbenzenesulphonate | longer than 2 h 30 |
| Sodium Lauryldiethoxyethylsulphate | approx. 1 h 30 |
| p-Octylphenylnonaethoxyethanol | approx. 1 h |
| Alkylbetaine | 10 to 20 min |

TABLE I-continued

| Product | Length of life of cercariae in the presence of 1 ppm of the product |
|---|---|
| Alkylamidobetaine | 5–15 min |

TABLE II

| Medium | Dilution | Contact Time | No. of inactivated schistosomae | % C.I. | No. of adult parasites after 7 weeks | % | No. of eggs per mg of liver | |
|---|---|---|---|---|---|---|---|---|
| Control | — | — | 0 | 0 | 56-89-71-63-60 54-78-69-60-56 | 45.2% 42.26% | | |
| Octarox 1030 | 6 ppm | 0 15 mins | 75-87-90-78-92 120-115-110-113-121 | 56.26% 77.33% | 0-8-12-10-2 7-8-3-2-7 | 5.33% 3.6% | 258-275 229-244-415-36-0 | 266 184 |
| Perolene LD | 2 ppm | 0 15 mins | 9-14-18-25-7 30-42-36-37-113 | 9.86% 34.4% | 12-21-13-4-20 19-18-24-0-14 | 9.33% 10% | 392-345-358-155-252 612-1059-933-0-886 | 300 698 |
| Amonyl 265 BA | 1.3 ppm | 15 mins 60 mins | 136-94-111-98-125 147-112-108-127-146 | 74% 85.6% | 0-0-0-0-0 0-0-0-0-0 | 0 0 | 0-0-0-0-0 0-0-0-0-0 | 0 0 |

What is claimed is:

1. A method for combating the cercariae which are the causative organisms of bilharziasis, which comprises contacting said cercariae with at least one amphoteric surface active agent of the betaine or imidazoline type, said amphoteric surface active agent being present in an amount effective to combat the said cercariae.

2. A method according to claim 1, wherein the contacting is achieved by pouring a quantity of surface active agent into water containing the said cercariae in such a quantity that the concentration of the said agent in the water is from 0.5 to 10 ppm inclusive.

3. A method according to claim 1, wherein the said contacting is achieved by dissolving or dispersing into the water containing the said cercariae a washing product which contains a sufficient quantity of surface active agent so that the concentration of the said agent in the water is from 0.5 to 10 ppm.

4. A method according to claim 3, wherein the said washing product is a toilet or household soap cake.

* * * * *